(12) United States Patent
Kihara

(10) Patent No.: US 9,739,756 B2
(45) Date of Patent: Aug. 22, 2017

(54) DATA PROCESSING SYSTEM AND METHOD FOR CHROMATOGRAPH

(71) Applicant: SHIMADZU CORPORATION, Kyoto-shi, Kyoto (JP)

(72) Inventor: Takayuki Kihara, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 723 days.

(21) Appl. No.: 14/246,454

(22) Filed: Apr. 7, 2014

(65) Prior Publication Data

US 2014/0303904 A1    Oct. 9, 2014

(30) Foreign Application Priority Data

Apr. 9, 2013  (JP) ................................ 2013-081159
Nov. 8, 2013  (JP) ................................ 2013-232043

(51) Int. Cl.
*G01N 31/00*   (2006.01)
*G01N 30/86*   (2006.01)
*G06F 11/30*   (2006.01)

(52) U.S. Cl.
CPC ................................ *G01N 30/8679* (2013.01)

(58) Field of Classification Search
CPC ................................................ G01N 30/8679
See application file for complete search history.

(56) References Cited

U.S. PATENT DOCUMENTS 7,225,360 B2 * 5/2007 Kihara ............... G01N 30/88 709/224
9,460,901 B2 * 10/2016 Kawase ............. H01J 49/0036

OTHER PUBLICATIONS

Dai Juuroku Kaisei Nihon Yakkyokuhou, "The Japanese Pharmacopeia, Sixteenth Edition", the Ministry of Health, Labor and Welfare, Mar. 24, 2011, <URL: http://jpdb.nihs.go.jp/jp16/>.

\* cited by examiner

*Primary Examiner* — Phuong Huynh
(74) *Attorney, Agent, or Firm* — Sughrue Mion, PLLC

(57) ABSTRACT

Based on three-dimensional data of time, wavelength and intensity acquired with a three-dimensional chromatograph, whether or not the peak-top intensity of the peak of a target component exceeds a predetermined upper limit is determined. If the intensity exceeds the limit, two wavelengths $\lambda 1$ and $\lambda 2$ are set in a spectrum passing through the peak top, where $\lambda 1$ is the peak-top wavelength while $\lambda 2$ is a wavelength which belongs to the peak and at which the intensity is within a predetermined range. For each point in time belonging to the target peak, the ratio between the intensity at $\lambda 1$ and the intensity at $\lambda 2$ in the spectrum at that point in time is calculated, and one of the calculated intensity ratios is selected as a correction value. Based on this correction value and a quantitative value calculated from a chromatogram at $\lambda 2$, the quantitative value of the target component is determined.

8 Claims, 6 Drawing Sheets

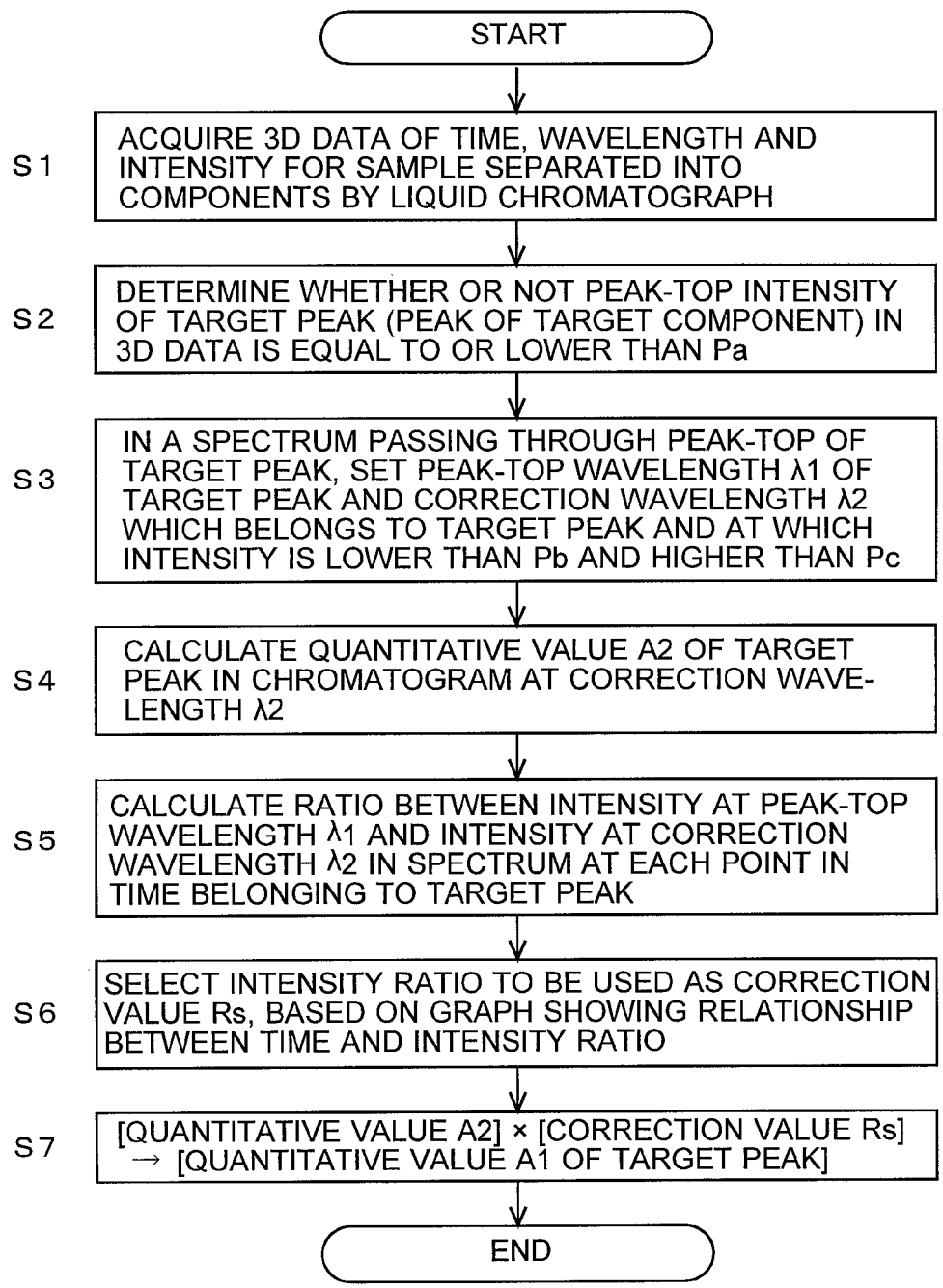

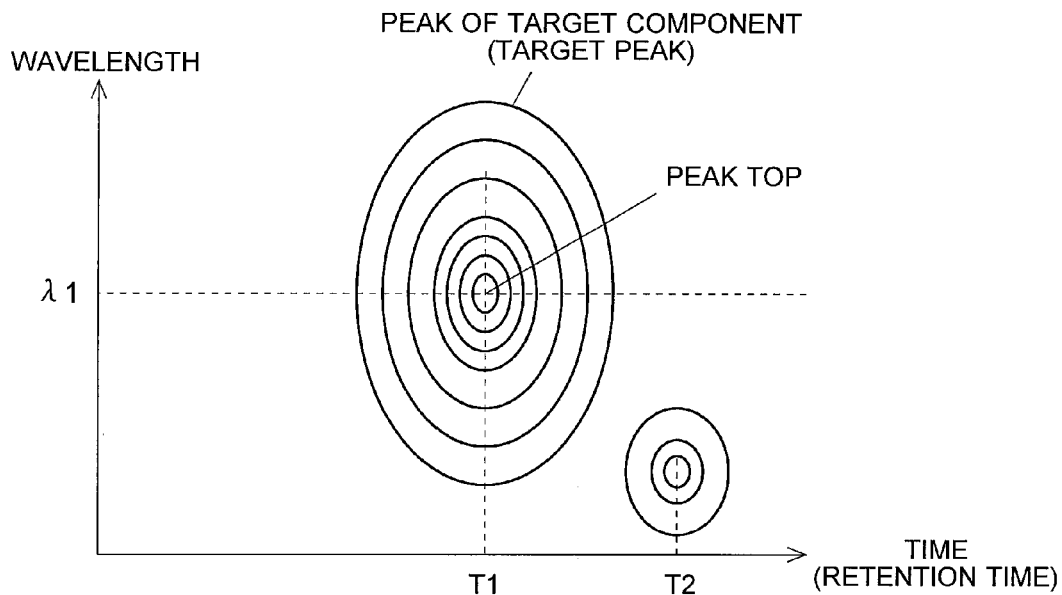
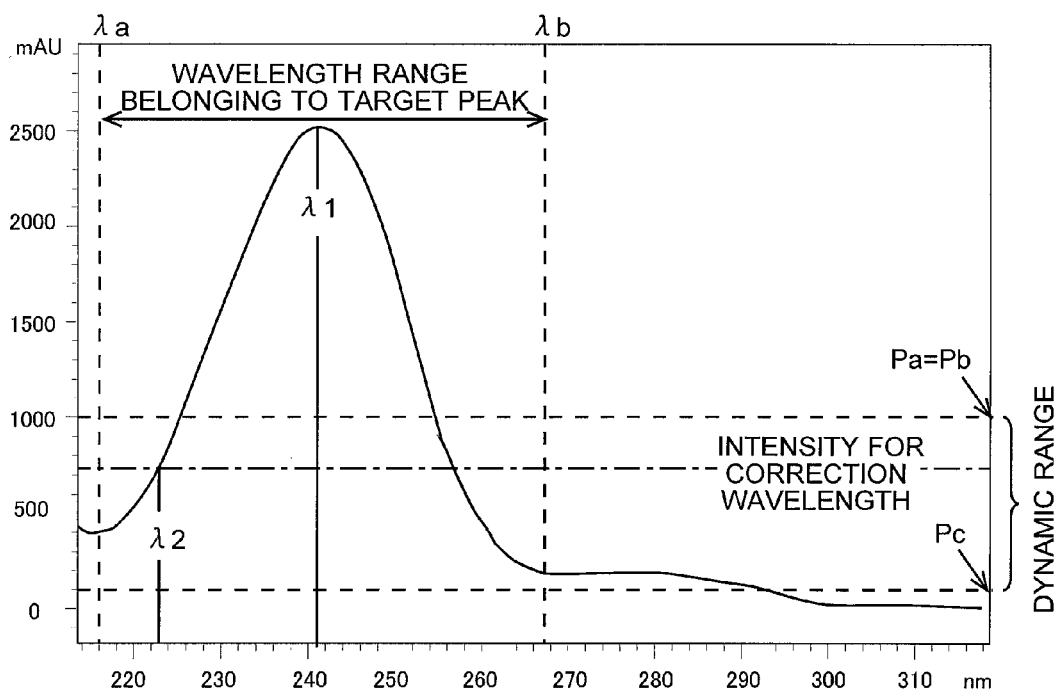

DATA PROCESSING SYSTEM AND METHOD FOR CHROMATOGRAPH

TECHNICAL FIELD

The present invention relates to a data processing system and a data processing method for a chromatographic apparatus, such as a liquid chromatograph or a gas chromatograph.

BACKGROUND ART

A chromatographic apparatus is a device for analyzing a sample to obtain a set of data representing a chromatogram which shows a signal intensity (e.g. output voltage) with respect to time (such a set of data are hereinafter called "chromatogram data"). A data processing system for a chromatograph processes the chromatogram data to detect each peak appearing on the chromatogram, identify a substance (component) corresponding to the detected peak by comparing the position (retention time) of that peak with a preset identification table, and calculate the concentration and/or amount of that substance (component) from the height or area of that peak. Such a data processing system (or method) is hereinafter called the "chromatographic data processing system (or method)."

Chromatographic data processing systems normally have some limits of the signal level that can be processed, due to hardware limitations on the signal-processing circuits including an A/D converter. For an input of a signal whose level is above the upper limit or below the lower limit, the system cannot perform correct calculations.

Apart from such a limit on the signal processing, it should also be noted that the reliability of a detection result obtained with a detector for a chromatographic apparatus varies depending on the signal level. For example, in a device used as a detector for a liquid chromatograph (e.g. an ultraviolet-visible spectrophotometer or a photo diode array detector), the non-linearity of the signal intensity normally becomes more noticeable as the component concentration in the sample increases, as shown in FIG. 9, which lowers the accuracy of quantitative determination. Meanwhile, the signal inevitably has various noises superposed on it. To deal with such a situation, it is preferable to dilute the sample before an analysis so that the concentration of each component in the sample will fall within a predetermined range (dynamic range).

CITATION LIST

Non-Patent Literature

Non-Patent Literature 1: "Dai Juuroku Kaisei Nihon Yakkyokuhou (The Japanese Pharmacopeia, Sixteenth Edition)", the Ministry of Health, Labor and Welfare, Mar. 24, 2011

SUMMARY OF INVENTION

Technical Problem

One of the applications of liquid chromatographs is an impurity analysis for analyzing the proportion of an impurity relative to a principal component. For example, impurity analyses are frequently performed for drugs or similar products.

In the case of analyzing a plurality of components contained in a sample, if the concentrations of the target components do not significantly differ from each other, it is possible to set the dilution ratio of the sample, the sensitivity of the detector and other parameters so that all the target components will fall within the dynamic range. However, if the concentrations of the target components are extremely different, it may be impossible to correctly detect all the components no matter what the setting is; that is to say, a setting for correctly detecting a component whose concentration in the sample is the lowest may lead to a distortion or saturation of the signal corresponding to a component whose concentration in the sample is the highest (principal component), while a setting for correctly detecting the highest-concentration component may cause the lowest-concentration component (impurity) to be obscured by noises.

For example, the Japanese Pharmacopeia, Sixteenth Edition (Non-Patent Literature 1) includes descriptions on the purity of acetylcysteine products, which states that the substances (impurities) other than acetylcysteine should satisfy the requirements that the peak area of each substance as calculated by the area percentage method should not be higher than 0.3% and the total area of the peaks of those substances should not be higher than 0.6% on a chromatogram obtained by a test using a liquid chromatograph connected to an ultraviolet absorptiometer with the measurement wavelength set at 220 nm ("Acetylcysteine: Purity (6) Related Substances", pp. 311-312 in the Japanese version, or pp. 322-323 in the English version, of the Japanese Pharmacopeia, Sixteenth Edition, both versions published on the website of the Ministry of Health, Labor and Welfare). In one conventional method for correctly measuring the concentration ratio of the components with such a large difference in concentration, a sample with a low dilution ratio and a sample with a high dilution ratio are prepared, and the measurement results obtained by performing an analysis multiple times are corrected according to the dilution ratios to determine the concentrations (or ratios of concentration) of the target components. In another conventional method, two cells with different optical path lengths are respectively set in two detectors so as to correct the optical path lengths so that the concentrations (or ratios of concentration) of the target components can be determined by a single analysis.

Even in the case of analyzing a single component, if its concentration beforehand is unknown, the detected intensity may possibly exceed the dynamic range. In such a case, it has conventionally been necessary to adjust the dilution ratio of the sample, the sensitivity of the detector and other parameters and once more perform the measurement.

The problem to be solved by the present invention is to provide a chromatographic data processing system and a chromatographic data processing method by which the concentration (or ratio of concentration) of each of the target components can be determined over a broad range of absorbance by a single analysis and with a single detector.

Solution to Problem

A data processing system for a chromatograph according to the first aspect of the present invention aimed at solving the previously described problem is a system for processing the three-dimensional data of time, wavelength and intensity acquired with a three-dimensional chromatograph, including:

a) a setting section for setting two wavelengths $\lambda 1$ and $\lambda 2$ in a spectrum passing through the peak top of a peak of a target component, based on the three-dimensional data, where $\lambda 1$ is a wavelength of the peak top while $\lambda 2$ is a wavelength which belongs to the peak and is different from $\lambda 1$;

b) a calculating section for calculating, for each of the points in time belonging to the peak, an intensity ratio between an intensity at the peak-top wavelength $\lambda 1$ and an intensity at the wavelength $\lambda 2$ in the spectrum obtained at that point in time;

c) an automatic correction-value selecting section for selecting, as a correction value, one of the intensity ratios respectively calculated for the aforementioned points in time by the calculating section; and d) a component quantity determining section for determining a quantitative value of the target component, based on the correction value and a quantitative value of the peak in a chromatogram at the wavelength $\lambda 2$.

A data processing system for a chromatograph according to the second aspect of the present invention aimed at solving the previously described problem is a system for processing the three-dimensional data of time, wavelength and intensity acquired with a three-dimensional chromatograph, including:

a) a setting section for setting two wavelengths $\lambda 1$ and $\lambda 2$ in a spectrum passing through the peak top of a peak of a target component, based on the three-dimensional data, where $\lambda 1$ is a wavelength of the peak top while $\lambda 2$ is a wavelength which belongs to the peak and is different from $\lambda 1$;

b) a calculating section for calculating, for each of the points in time belonging to the peak, an intensity ratio between an intensity at the peak-top wavelength $\lambda 1$ and an intensity at the wavelength $\lambda 2$ in the spectrum obtained at that point in time;

c) a graphic displaying section for displaying a graphic image showing a relationship between the intensity ratio and the point in time of the spectrum for which the intensity ratio has been calculated;

d) a correction-value selecting section for allowing a user to select, as a correction value, one of the intensity ratios shown on the graphic image; and e) a component quantity determining section for determining a quantitative value of the target component, based on the correction value and a quantitative value of the peak in a chromatogram at the wavelength $\lambda 2$.

In one preferable mode of the first or second aspect of the present invention, the system further includes a determining section for determining whether or not the peak-top intensity of the peak of the target component exceeds a predetermined upper limit, and the setting section sets the two wavelengths $\lambda 1$ and $\lambda 2$ in the case where the peak-top intensity exceeds the upper limit.

In this case, the setting section may preferably set the wavelength $\lambda 2$ at a wavelength at which the intensity is equal to or lower than a predetermined upper limit as well as equal to or higher than a predetermined lower limit.

Both the "predetermined upper limit" used in the determining section and that used in the setting section should normally be set at the upper limit of the dynamic range, although it is possible to use a lower and securer value or a slightly higher value which is practically acceptable.

The "predetermined lower limit" used in the setting section should normally be set at the lower limit of the dynamic range, although it is also possible to choose a slightly higher value.

The "predetermined upper limit" used in the determining section and that used in the setting section may be equal to or different from each other.

The "peak-top wavelength" should normally be a wavelength corresponding to the peak top of the peak of the target component, although it may be any wavelength in the vicinity to the peak top.

The "quantitative value" is a peak height or a peak area of a chromatogram peak.

In the second aspect of the present invention, the correction value selected by the correction-value selecting section may be displayed on the aforementioned graphic image.

A spectrum of a component inherently has a shape specific to that component. This shape should not change depending on the level of the concentration of the component. Such a similarity in the spectrum shape yields a certain mutual relationship among the quantitative values of the chromatogram peaks respectively observed at different wavelengths belonging to the same peak. By using this relationship, the quantitative value of a target component to be calculated from a chromatogram peak at the peak-top wavelength $\lambda 1$ can be computed from the quantitative value of a chromatogram peak at another wavelength $\lambda 2$ which belongs to the same peak. However, if a significant error is contained in the intensity at the peak-top wavelength $\lambda 1$ or the second wavelength $\lambda 2$ (e.g. if the intensity at the peak-top wavelength $\lambda 1$ and/or the intensity at the second wavelength $\lambda 2$ is outside the dynamic range), the spectrum at that point in time will lose its original shape, which causes the two intensities calculated at that point in time to deviate from the aforementioned relationship. To avoid this situation, a specific criterion should be provided so as to use a relationship determined in a time range where the error is acceptably small.

In the chromatographic data processing system according to the first aspect of the present invention, two wavelengths $\lambda 1$ and $\lambda 2$ are initially set in a spectrum passing through the peak top of the peak of the target component on the three-dimensional data, where $\lambda 1$ is a wavelength of the peak top while $\lambda 2$ is a wavelength which belongs to the peak and is different from $\lambda 1$. Additionally, the system can also be configured so as to set the peak-top wavelength $\lambda 1$ and the second wavelength $\lambda 2$ and calculate a correction value (as will be described later) only when the peak-top intensity of the peak of the target component exceeds the upper limit of the dynamic range, while using a normal method to calculate the quantitative value of the target component from the chromatogram peak at the peak-top wavelength $\lambda 1$ when the peak-top intensity does not exceed the upper limit.

Next, in the spectrum passing through the peak top, the peak-top wavelength $\lambda 1$ and another wavelength $\lambda 2$ belonging to the target component are set. As already stated, this second wavelength $\lambda 2$ is a wavelength at which the intensity is within the dynamic range. Accordingly, the quantitative value of the peak of the target component in the chromatogram at the wavelength $\lambda 2$ can be calculated with high accuracy.

Subsequently, for each of the points in time belonging to the peak of the target component, the ratio between the intensity at the peak-top wavelength $\lambda 1$ and the intensity at the other wavelength $\lambda 2$ in the spectrum obtained at that point in time is calculated. Then, according to a predetermined selection criterion, one of the intensity ratios within a time range where the error of the intensity at $\lambda 1$ or that of the intensity at $\lambda 2$ is small is selected as the correction value.

The correction value thus selected and the quantitative value of the peak of the target component determined in the chromatogram at the wavelength λ2 can be obtained with high accuracy. Therefore, by using these values, the quantitative value of the peak in the chromatogram at the wavelength λ1 (the quantitative value of the target component) can be calculated with high accuracy.

Thus, in the chromatographic data processing system according to the first aspect of the present invention, the dynamic range can be effectively expanded. In the case where a sample containing a high-concentration component and a low-concentration component mixed together is analyzed using a chromatographic apparatus capable of acquiring three-dimensional data, the measurement for the two components can be performed in a single analysis and with a single detector. Furthermore, in the case of analyzing a single component whose concentration in the sample is unknown, the measurement can be performed in a single analysis and with a single detector by expanding the dynamic range.

The automatic correction-value selecting section should preferably select, as the correction value, one of the intensity ratios obtained within a time range where both the intensity at the peak-top wavelength λ1 and the intensity at the second wavelength λ2 are within the dynamic range, and more preferably, to select the highest intensity ratio obtained under the conditions that the two intensities are within the dynamic range. Within a time range where both the intensity at the peak-top wavelength λ1 and the intensity at the second wavelength λ2 are within the dynamic range, the intensity ratio monotonically increases, approaching a certain constant value. This means that the intensity ratio that is the highest within this time range most accurately indicates the similarity of the spectra. Accordingly, the quantitative value of the target component can be calculated with high accuracy by using the highest value of the intensity ratio as the correction value.

In the chromatographic data processing system according to the second aspect of the present invention, a graph showing a relationship between time and intensity ratio is displayed on a monitor or similar device to allow a user to select one of the intensity ratios as the correction value. Preferably, the user should select one value from a time range where the intensity ratio has a constant value, whereby the quantitative value of the target compound can be calculated with high accuracy as in the case of the chromatographic data processing system according to the first aspect of the present invention.

Chromatographic data processing methods according to the third and fourth aspects of the present invention are method versions of the present invention based on the same technical ideas as the first and second aspects of the present invention. Specifically, the chromatographic data processing method according to the third aspect of the present invention includes:

a) a setting step, in which two wavelengths λ1 and λ2 in a spectrum passing through the peak top of a peak of a target component are set based on the three-dimensional data of time, wavelength and intensity acquired with a three-dimensional chromatograph, where λ1 is a wavelength of the peak top while λ2 is a wavelength which belongs to the peak and is different from λ1;

b) an intensity ratio calculating step, in which, for each of the points in time belonging to the peak, an intensity ratio between an intensity at the peak-top wavelength λ1 and an intensity at the wavelength λ2 is calculated in the spectrum obtained at that point in time;

c) an automatic correction-value selecting step, in which one of the intensity ratios respectively calculated for the aforementioned points in time in the intensity ratio calculating step is selected as a correction value; and d) a component quantity determining step, in which a quantitative value of the target component is determined based on the correction value and a quantitative value of the peak in a chromatogram at the wavelength λ2.

The chromatographic data processing method according to the fourth aspect of the present invention includes:

a) a setting step, in which two wavelengths λ1 and λ2 in a spectrum passing through the peak top of a peak of a target component are set based on the three-dimensional data of time, wavelength and intensity acquired with a three-dimensional chromatograph, where λ1 is a wavelength of the peak top while λ2 is a wavelength which belongs to the peak and is different from λ1;

b) an intensity ratio calculating step, in which, for each of the points in time belonging to the peak, an intensity ratio between an intensity at the peak-top wavelength λ1 and an intensity at the wavelength λ2 is calculated in the spectrum obtained at that point in time;

c) a graphic displaying step, in which a graphic image showing a relationship between the intensity ratio and the point in time of the spectrum for which the intensity ratio has been calculated is displayed;

d) a correction value selecting step, in which a user is allowed to select, as a correction value, one of the intensity ratios shown on the graphic image; and e) a component quantity determining step, in which a quantitative value of the target component is determined based on the correction value and a quantitative value of the peak in a chromatogram at the wavelength λ2.

Advantageous Effects of Invention

With the chromatographic data processing system and the chromatographic data processing method according to the present invention, the concentrations (or ratios of concentration) of target components can be determined over a broad range of absorbance by a single analysis and with a single detector. Accordingly, the analysis can be completed in a shorter period of time. Additionally, the system has a simpler construction and is advantageous for reducing expenses.

BRIEF DESCRIPTION OF THE DRAWINGS

FIG. 2 is a schematic flowchart of the data processing performed in the chromatographic data processing system of the present embodiment.

FIG. 3 is a contour diagram showing three-dimensional data to be obtained by the chromatographic data processing system of the present embodiment.

FIG. 4 is a spectrum obtained from the three-dimensional data along the line of time=T1.

DESCRIPTION OF EMBODIMENTS

One embodiment of the chromatographic data processing system according to the present invention is hereinafter specifically described with reference to the attached drawings.

EXAMPLE

Figure 1:
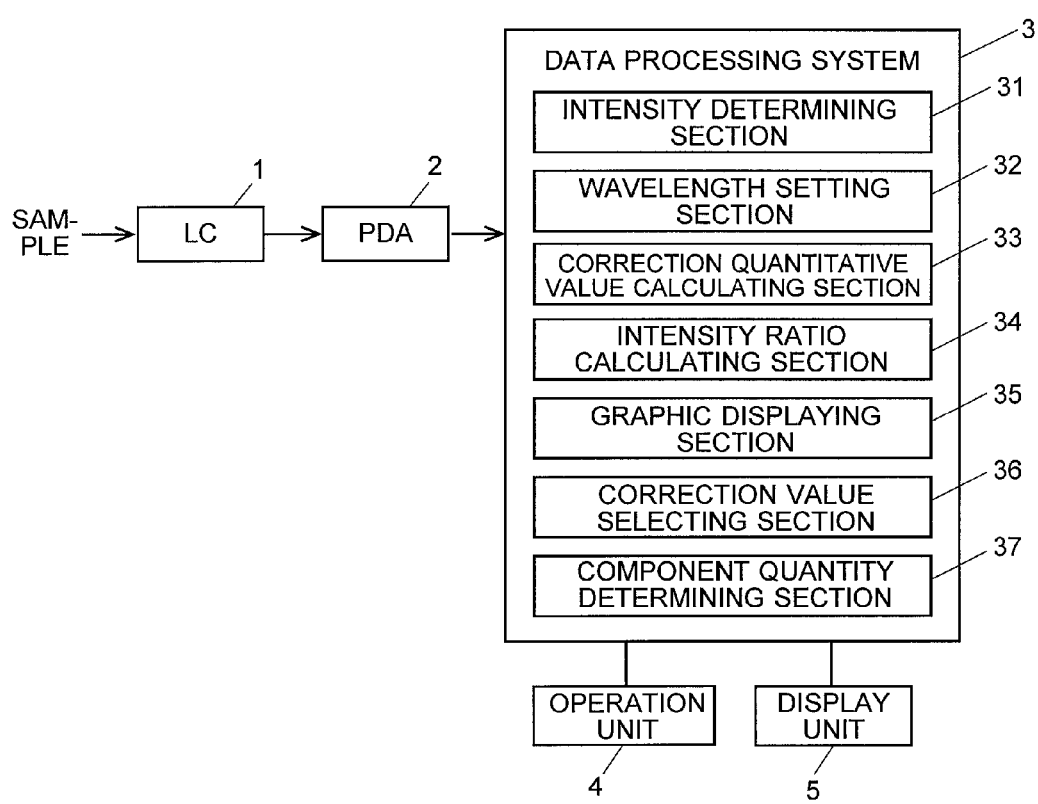
FIG. 1 is a schematic configuration diagram of an analyzing system including a chromatographic data processing system as one embodiment of the present invention.

FIG. 1 is a schematic configuration diagram of an analyzing system including a chromatographic data processing system according to the present embodiment. This analyzing system includes a liquid chromatograph (LC) 1 for temporally separating the components contained in a liquid sample, a photo diode array detector (PDA) 2 for detecting spectra of each of the separated components over a predetermined range of wavelengths, and a data processing system 3 for processing data produced by the PDA 2. The substance of the data processing system 3 is a commonly used computer having a CPU (central processing unit), a memory device (e.g. RAM, HDD or SSD) and other devices. This computer has a dedicated data-processing software program installed. By executing this program, various functions as shown in FIG. 1 are realized, such as the intensity determining section 31, the wavelength setting section 32, the correction quantitative value calculating section 33, the intensity ratio calculating section 34, the graphic displaying section 35, the correction value selecting section 36, and the component quantity determining section 37.

Additionally, an operation unit 4 (e.g. a keyboard and a mouse or similar pointing device) and a display unit 5 are connected to the data processing system 3.

A process of calculating the quantitative value of a target component is hereinafter described with reference to the flowchart shown in FIG. 2. Initially, a target sample to be analyzed is introduced into the LC 1, which temporally separates the components contained in the sample. The obtained components are individually detected by the PDA 2. The detection data are sequentially sent to the data processing system 3, which produces three-dimensional data of time, wavelength and intensity as shown in FIG. 3 (Step S1). The intensity determining section 31 in the data processing system 3 determines whether or not the peak-top intensity of the peak of the target component in the three-dimensional data (which is hereinafter called the "target peak") exceeds a predetermined upper limit Pa (Step S2). This upper limit Pa is a value which has been preset in the data processing system 3 taking into account the dynamic range of the PDA 2, the A/D converter (not shown) and other elements. Normally, the upper limit of the dynamic range is used as Pa, although it is possible to use a lower and securer value or a slightly higher value which is practically acceptable.

In Step S2, if the peak-top intensity of the target peak has been found to be equal to or lower than the upper limit Pa, the data processing system 3 calculates the quantitative value (peak area or peak height) of the target component by a normal method from the chromatogram taken along the peak-top wavelength λ1 of the target peak, and completes the entire calculation without performing the processes of Step S3 through S7.

If the peak-top intensity of the target peak has been found to be higher than the upper limit Pa, the quantitative value of the target component calculated from the chromatogram taken along the peak-top wavelength λ1 of the target peak will not be a correct value. Therefore, the operation proceeds to Step S3 to perform a correction of the quantitative value of the target component as follows.

In Step S3, two wavelengths λ1 and λ2 are set within a wavelength range which belongs to the target peak in the spectrum passing through the peak top of the target peak (i.e. the spectrum taken along the line of time=T1 in FIG. 3), where λ1 is the peak-top wavelength and λ2 is another wavelength at which the intensity is equal to or lower than a predetermined upper limit Pb as well as equal to or higher than a predetermined lower limit Pc, as shown in FIG. 4 (λ2 is hereinafter called the "correction wavelength"). Similar to the upper limit Pa, the upper limit Pb is a value which has been preset in the data processing system 3 based on the upper limit of the dynamic range of the PDA 2 and other elements. The upper limits Pa and Pb respectively used in Steps S2 and S3 may be equal to or different from each other. In the present embodiment, Pa=Pb.

The lower limit Pc is a value which has been preset in the data processing system 3 based on the lower limit of the aforementioned dynamic range. Pc should normally be set at the lower limit of the dynamic range, although a slightly higher value may also be used.

Figure 5:
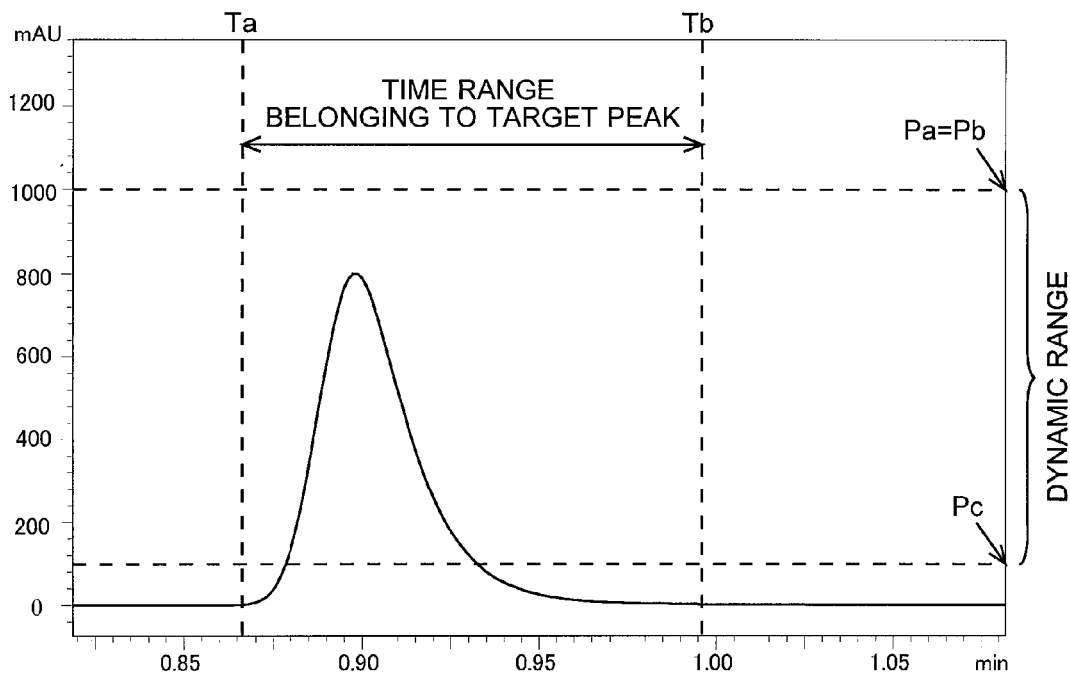
FIG. 5 is a chromatogram obtained from the three-dimensional data along the line of correction wavelength=λ2.

The correction quantitative value calculating section 33 creates a chromatogram at the correction wavelength λ2 (correction chromatogram) from the three-dimensional data (FIG. 5), and then calculates, as the correction quantitative value, a quantitative value A2 (peak area or peak height) of the chromatogram peak corresponding to the target peak in this correction chromatogram (Step S4). Since the maximum value of the chromatogram peak is not higher than the upper limit of the dynamic range, the quantitative value of this peak can correctly be calculated.

Figure 6:
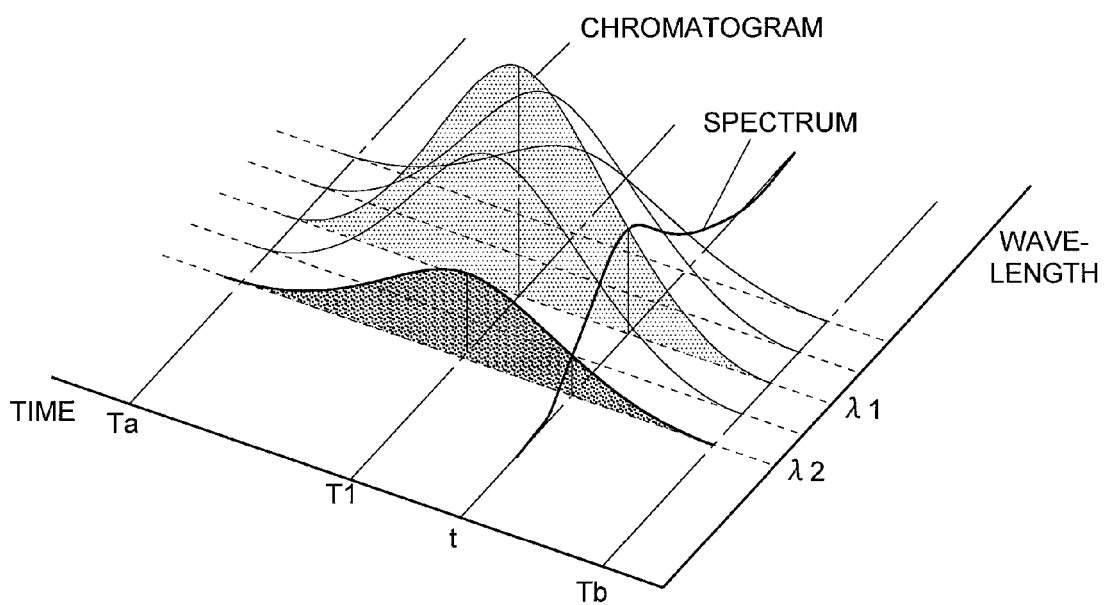
FIG. 6 is a three-dimensional graph of time-wavelength-intensity showing the concept of the process for calculating an intensity ratio.
Figure 7:
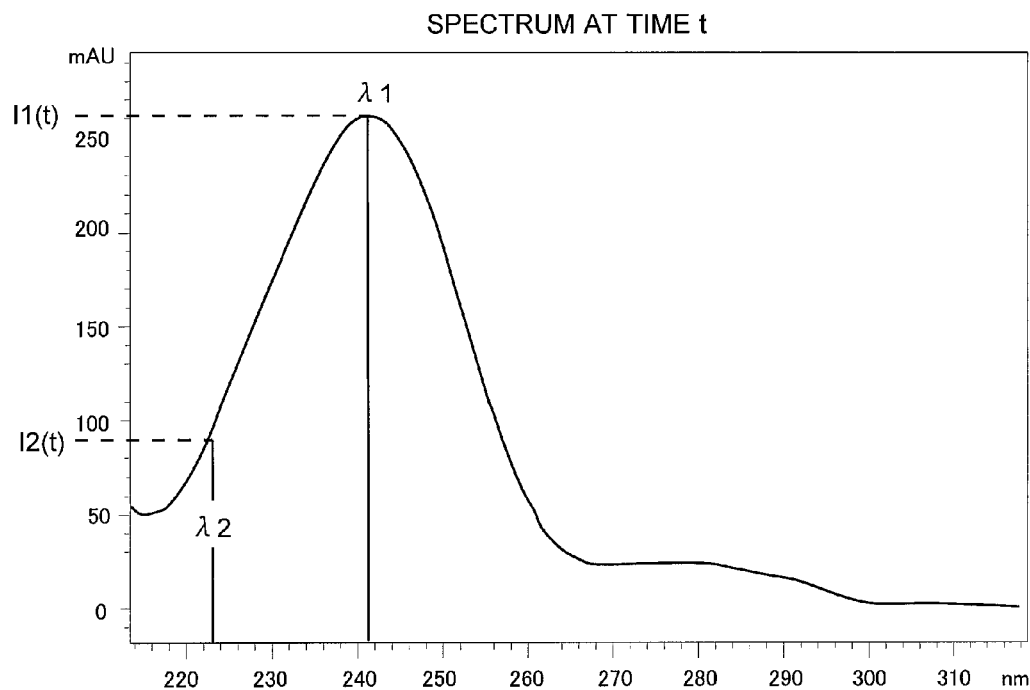
FIG. 7 is a spectrum at time t belonging to a target peak.

At each point in time t within a time range of [Ta, Tb] belonging to the target peak (FIGS. 5 and 6), the intensity ratio calculating section 34 acquires an intensity $I_1(t)$ at the wavelength λ1 and an intensity $I_2(t)$ at the correction wavelength λ2 (FIG. 7), and calculates an intensity ratio R(t) as follows (Step S5):

$$R(t)=I_1(t)/I_2(t)$$

Figure 8:
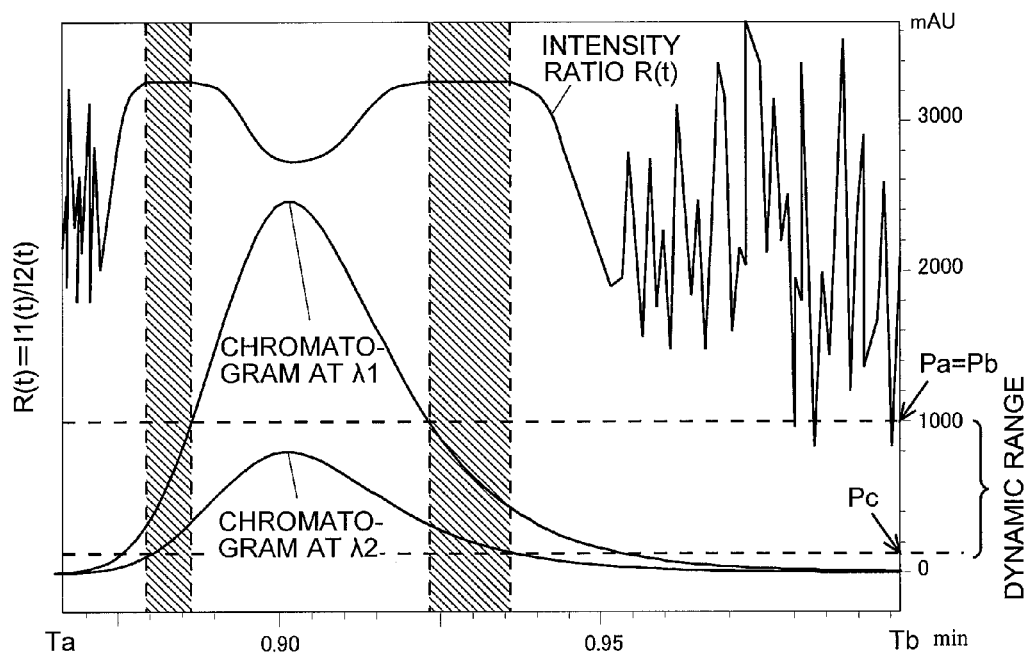
FIG. 8 is a graph showing a relationship between time and intensity ratio as well as two chromatograms respectively obtained at the peak-top wavelength λ1 and the correction wavelength λ2.
Figure 9:
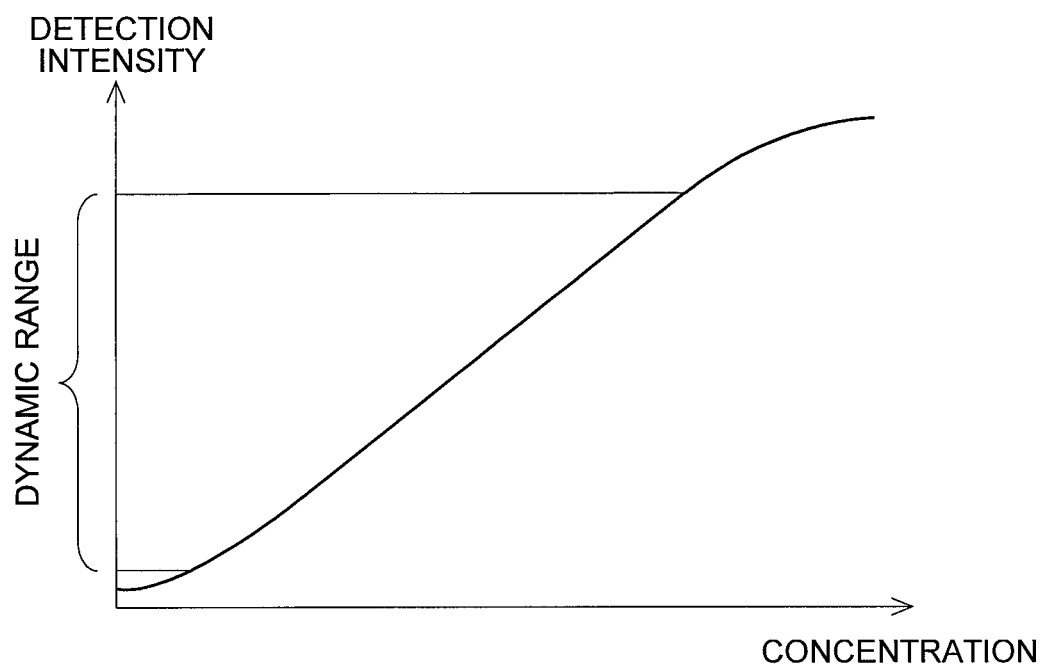
FIG. 9 is an explanatory diagram showing the dynamic range in a detector.

The graphic displaying section 35 creates a graph of this intensity ratio R(t) and shows it on the display unit 5. As shown in FIG. 8, when at least one of the intensities $I_1(t)$ and $I_2(t)$ is out of the dynamic range, the similarity of the spectrum shape is violated and the intensity ratio R(t) deviates from the constant value. By contrast, when both of the intensities $I_1(t)$ and $I_2(t)$ are within the dynamic range, the intensity ratio R(t) is almost constant. Accordingly, when both of the intensities $I_1(t)$ and $I_2(t)$ are within the dynamic range, the similarity between the spectra is at the highest level, which means that the spectra are highly reliable. In the present embodiment, the correction value selecting section 36 automatically sets, as the correction value Rs, the average (mean, median or mode) of the intensity ratios R(t) obtained within a time range where both of the intensities $I_1(t)$ and $I_2(t)$ are within the dynamic range.

With the correction value Rs thus set, the component quantity determining section 37 calculates the quantity value A1 of the target peak. Specifically, as expressed by the following equation, the quantity value A1 is calculated by multiplying the quantity value A2 obtained from the chromatogram at the correction wavelength λ2 in Step S4 by the correction value Rs (Step S7):

$$A1=A2\times Rs$$

Thus, a correct quantitative value A1 of the target peak can be calculated using the quantitative value A2 determined within the dynamic range of the PDA 2 and the correction value Rs.

The correction value selecting section 36 may be configured so as to allow users to select one of the intensity ratios on the graph of the intensity ratio R(t) shown on the display unit 5 instead of automatically setting the correction value Rs.

The correction wavelength λ2 may automatically be set by the wavelength setting section 32 based on the three-dimensional data. A method for automatically setting the correction wavelength λ2 is as follows:

A spectrum of the target peak at retention time T1 is acquired.

In this spectrum, a wavelength at which the intensity value on the positive (longer-wavelength) side or negative (shorter-wavelength) side of the peak-top wavelength λ1 exceeds an "intensity for the correction wavelength" preset by the user is selected as the correction wavelength λ2 (FIG. 4). The searching direction (positive or negative) can be selected previously by the user or preset in the system (in FIG. 4, the search is made in the negative direction).

In the previous embodiment, whether or not the peak-top intensity of the peak of the target component exceeds the upper limit Pa is determined and the processes of Steps S3 through S7 are performed only when the intensity exceeds the upper limit. However, it is also possible to always perform those processes.

REFERENCE SIGNS LIST

1 . . . Liquid Chromatograph (LC)
2 . . . Photo Diode Array Detector (PDA)
3 . . . Data Processing System
   31 . . . Intensity Determining Section
   32 . . . Wavelength Setting Section
   33 . . . Correction Quantitative Value Calculating Section
   34 . . . Intensity Ratio Calculating Section
   35 . . . Graphic Displaying Section
   36 . . . Correction Value Selecting Section
   37 . . . Component Quantity Determining Section
4 . . . Operation Unit
5 . . . Display Unit

The invention claimed is:

1. A three-dimensional chromatograph, comprising:
a three-dimensional chromatograph part that temporally separates components contained in a sample, the separated components including a target component;
a detector that detects the separated components; and
a data processing system that produces three-dimensional data of time, wavelength and intensity acquired with the three-dimensional chromatograph part based on the detected separated components, the data processing system including,
  a) a setting section for setting two wavelengths λ1 and λ2 in a spectrum passing through a peak top of a peak of the target component, based on the three-dimensional data, where λ1 is a wavelength of the peak top while λ2 is a wavelength which belongs to the peak and is different from λ1;
  b) a calculating section for calculating, for each of points in time belonging to the peak, an intensity ratio between an intensity at the peak-top wavelength λ1 and an intensity at the wavelength λ2 in a spectrum obtained at that point in time;
  c) an automatic correction-value selecting section for selecting, as a correction value, one of the intensity ratios respectively calculated for the aforementioned points in time by the calculating section; and
  d) a component quantity determining section for determining a quantitative value of the target component, based on the correction value and a quantitative value of the peak in a chromatogram at the wavelength λ2.

2. The three-dimensional chromatograph according to claim 1, wherein:
the data processing system further includes a determining section for determining whether or not the peak-top intensity of the peak of the target component exceeds a predetermined upper limit; and
the setting section sets the wavelength λ1 of the peak-top and the wavelength λ2 in the case where the peak-top intensity exceeds the upper limit, the wavelength λ2 being set at a wavelength at which the intensity is equal to or lower than the upper limit as well as equal to or higher than a predetermined lower limit.

3. A three-dimensional chromatograph, comprising:
a three-dimensional chromatograph part that temporally separates components contained in a sample, the separated components including a target component;
a detector that detects the separated components; and
a data processing system that produces three-dimensional data of time, wavelength and intensity acquired with the three-dimensional chromatograph part based on the detected separated components, the data processing system including
  a) a setting section for setting two wavelengths λ1 and λ2 in a spectrum passing through a peak top of a peak of the target component, based on the three-dimensional data, where λ1 is a wavelength of the peak top while λ2 is a wavelength which belongs to the peak and is different from λ1;
  b) a calculating section for calculating, for each of points in time belonging to the peak, an intensity ratio between an intensity at the peak-top wavelength λ1 and an intensity at the wavelength λ2 in a spectrum obtained at that point in time;
  c) a graphic displaying section for displaying a graphic image showing a relationship between the intensity ratio and the point in time of the spectrum for which the intensity ratio has been calculated;
  d) a correction-value selecting section for allowing a user to select, as a correction value, one of the intensity ratios shown on the graphic image; and
  e) a component quantity determining section for determining a quantitative value of the target component, based on the correction value and a quantitative value of the peak in a chromatogram at the wavelength λ2.

4. The three-dimensional chromatograph according to claim 3, wherein:
the data processing system further includes a determining section for determining whether or not the peak-top intensity of the peak of the target component exceeds a predetermined upper limit; and
the setting section sets the wavelength λ1 of the peak-top and the wavelength λ2 in the case where the peak-top intensity exceeds the upper limit, the wavelength λ2 being set at a wavelength at which the intensity is equal to or lower than the upper limit as well as equal to or higher than a predetermined lower limit.

5. A three-dimensional chromatography method, comprising:
  temporally separating components contained in a sample using a chromatograph part, the separated components including a target component;
  detecting the separated components;
  producing three-dimensional data of time, wavelength and intensity acquired with a three-dimensional chromatograph based on the detected separated components,
  a) setting two wavelengths $\lambda 1$ and $\lambda 2$ in a spectrum passing through a peak top of a peak of the target component based on the three-dimensional data of time, wavelength and intensity acquired with the three-dimensional chromatograph part, where $\lambda 1$ is a wavelength of the peak top while $\lambda 2$ is a wavelength which belongs to the peak and is different from $\lambda 1$;
  b) calculating, for each of points in time belonging to the peak, an intensity ratio between an intensity at the peak-top wavelength $\lambda 1$ and an intensity at the wavelength $\lambda 2$ in a spectrum obtained at that point in time;
  c) automatically selecting one of the intensity ratios respectively calculated for the aforementioned points in time as a correction value; and
  d) determining a quantitative value of the target component based on the correction value and a quantitative value of the peak in a chromatogram at the wavelength $\lambda 2$.

6. The three-dimensional chromatography method according to claim 5, further comprising:
  determining step whether or not the peak-top intensity of the peak of the target component exceeds a predetermined upper limit; and
  wherein, in the setting step, the wavelength $\lambda 1$ of the peak-top and the wavelength $\lambda 2$ are set in the case where the peak-top intensity exceeds the upper limit, the wavelength $\lambda 2$ being set at a wavelength at which the intensity is equal to or lower than the upper limit as well as equal to or higher than a predetermined lower limit.

7. A three-dimensional chromatography method, comprising:
  temporally separating components contained in a sample using a chromatograph, the separated components including a target component;
  detecting the separated components;
  producing three-dimensional data of time, wavelength and intensity acquired with a three-dimensional chromatograph based on the detected separated components,
  a) setting two wavelengths $\lambda 1$ and $\lambda 2$ in a spectrum passing through a peak top of a peak of the target component based on the three-dimensional data of time, wavelength and intensity acquired with the three-dimensional chromatograph, where $\lambda 1$ is a wavelength of the peak top while $\lambda 2$ is a wavelength which belongs to the peak and is different from $\lambda 1$;
  b calculating, for each of points in time belonging to the peak, an intensity ratio between an intensity at the peak-top wavelength $\lambda 1$ and an intensity at the wavelength $\lambda 2$ in a spectrum obtained at that point in time;
  c) displaying a graphic image showing a relationship between the intensity ratio and the point in time of the spectrum for which the intensity ratio has been calculated;
  d) allowing a user is allowed to select, as a correction value, one of the intensity ratios shown on the graphic image; and
  e) determining a quantitative value of the target component based on the correction value and a quantitative value of the peak in a chromatogram at the wavelength $\lambda 2$.

8. The three-dimensional chromatography method according to claim 7, further comprising:
  determining whether or not the peak-top intensity of the peak of the target component exceeds a predetermined upper limit; and
  wherein, in the setting step, the wavelength $\lambda 1$ of the peak-top and the wavelength $\lambda 2$ are set in the case where the peak-top intensity exceeds the upper limit, the wavelength $\lambda 2$ being set at a wavelength at which the intensity is equal to or lower than the upper limit as well as equal to or higher than a predetermined lower limit.

* * * * *